United States Patent
Weber-Dabrowska et al.

(10) Patent No.: US 7,232,564 B2
(45) Date of Patent: Jun. 19, 2007

(54) METHODS OF POLYVALENT BACTERIOPHAGE PREPARATION FOR THE TREATMENT OF BACTERIAL INFECTIONS

(75) Inventors: Beata Weber-Dabrowska, Wroclaw (PL); Marian Mulczyk, Wroclaw (PL); Andrzej Gorski, Wroclaw (PL); Janusz Boratynski, Wroclaw (PL); Marzanna Lusiak-Szelachowska, Wroclaw (PL); Danuta Syper, Wroclaw (PL)

(73) Assignee: Instytut Immunologii I Terapii Doswiadczal-Nej Pan, Wroclaw (PL)

( * ) Notice: Subject to any disclaimer, the term of this patent is extended or adjusted under 35 U.S.C. 154(b) by 0 days.

(21) Appl. No.: 10/484,236

(22) PCT Filed: Jul. 18, 2002

(86) PCT No.: PCT/PL02/00053

§ 371 (c)(1), (2), (4) Date: Sep. 21, 2004

(87) PCT Pub. No.: WO03/008564

PCT Pub. Date: Jan. 30, 2003

(65) Prior Publication Data

US 2005/0032036 A1    Feb. 10, 2005

(30) Foreign Application Priority Data

Jul. 18, 2001 (PL) .................... 348740
Jun. 30, 2002 (PL) .................... 354822

(51) Int. Cl.
*C12N 7/00* (2006.01)
*C12Q 1/70* (2006.01)

(52) U.S. Cl. .............. 424/93.1; 435/5; 435/235.1

(58) Field of Classification Search .......... 424/93.6, 424/235.1, 184.1, 543, 93.1, 199.1; 435/239, 435/259, 235.1, 5
See application file for complete search history.

(56) References Cited

U.S. PATENT DOCUMENTS

| | | | | |
|---|---|---|---|---|
| 4,118,315 A | * | 10/1978 | Fletcher et al. | 210/638 |
| 4,797,363 A | * | 1/1989 | Teodorescu et al. | 435/235.1 |
| 4,828,999 A | * | 5/1989 | Jackson | 435/235.1 |
| 5,470,573 A | | 11/1995 | Lubitz et al. | |
| 5,824,468 A | | 10/1998 | Scherer et al. | |
| 5,846,604 A | * | 12/1998 | Caldwell | 427/245 |

(Continued)

FOREIGN PATENT DOCUMENTS

CS      192212      8/1979

(Continued)

OTHER PUBLICATIONS

Alonso, MC e tal, Microbiologia Sem. vol. 10, pp. 285-296, 1994, A direct membrane filter method for enumberating somatic coliphages in driinking water.*

(Continued)

*Primary Examiner*—Mark Navarro
*Assistant Examiner*—Ginny Allen Portner
(74) *Attorney, Agent, or Firm*—Clark & Elbing LLP

(57) ABSTRACT

The multivalent strains of bacteriophages, methods of obtaining these and their use in the treatment of bacterial infections, particularly those of drug-resistant bacterial strains, especially arising in mucoviscidosis patients, are provided.

8 Claims, 4 Drawing Sheets

*Staphylococcus*

845 strains employed in the study of 7 bacteriophages.

Number of Staph. strains *n* of a new sample for each phage

| Phage no.<br>1- α, d | 1 | 2 | 3 | 4 | 5 | 6 | 7 |
|---|---|---|---|---|---|---|---|
| 0.95, 0.1 | 56 | 24 | 37 | 93 | 93 | 61 | 89 |
| 0.95, 0.05 | 222 | 97 | 149 | 374 | 373 | 245 | 355 |
| 0.95, 10% *p* | 82 | 28 | 3144 | 535 | 538 | 1548 | 673 |
| 0.98, 0.1 | 66 | 29 | 44 | 111 | 111 | 73 | 108 |

U.S. PATENT DOCUMENTS

| | | | |
|---|---|---|---|
| 6,027,930 | A | 2/2000 | Borrebaeck |
| 6,121,036 | A * | 9/2000 | Ghanbari et al. ......... 435/235.1 |
| 6,322,783 | B1 | 11/2001 | Takahashi |
| 6,461,608 | B1 * | 10/2002 | Averback et al. .......... 424/93.6 |
| 6,482,632 | B1 * | 11/2002 | Agrawal et al. ......... 435/235.1 |
| 6,696,295 | B2 * | 2/2004 | Westpheling et al. ....... 435/472 |
| 6,783,930 | B1 * | 8/2004 | Pelletier et al. ................ 435/5 |
| 6,787,360 | B2 * | 9/2004 | Agrawal et al. ............ 435/473 |
| 2002/0127547 | A1 | 9/2002 | Miller |
| 2003/0216338 | A1 * | 11/2003 | Merril et al. .................. 514/44 |
| 2004/0247569 | A1 * | 12/2004 | Morris et al. .............. 424/93.6 |
| 2005/0107326 | A1 * | 5/2005 | Norris et al. .................. 514/44 |
| 2005/0175991 | A1 * | 8/2005 | Sulakvelidze et al. ......... 435/5 |
| 2005/0260171 | A1 * | 11/2005 | Ghanbari et al. .......... 424/93.6 |

FOREIGN PATENT DOCUMENTS

| | | |
|---|---|---|
| DE | 19828596 | 2/1999 |
| EP | 0290295 | 11/1988 |
| EP | 0414304 | 2/1991 |
| EP | 0510907 | 10/1992 |
| GB | 829266 | 3/1960 |
| GB | 2253859 | 9/1992 |
| GB | 2285684 | 7/1995 |
| RU | 2109055 | 4/1998 |
| SU | 543260 | 4/1984 |
| WO | WO 90/03122 | 4/1990 |
| WO | WO 94/06931 | 3/1994 |
| WO | WO 95/05454 | 2/1995 |
| WO | WO 96/07329 | 3/1996 |
| WO | WO 98/08944 | 3/1998 |
| WO | WO 01/00786 | 1/2001 |
| WO | WO 01/09370 | 2/2001 |

OTHER PUBLICATIONS

Konopka, M et al, ACTA Microbiologica Polonica, 1996, vol. 45, No. 3-4, pp. 269-278, Phenotyping methods in epidemiological analysis of Epidemic *Staphylococcus aureus* strains.*

Sulakvelidze, A et al, Antimicrobial Agents and Chemotherapy, Mar. 2001, vol. 45(3),pp. 649-659, Bacteriophage therapy, Minireview.*

Burroughs, NJ et al, Applied and Environmental Microbiology, Sep. 2000, vol. 66(9), pp. 3868-3877, Mathematical Analysis of growth and interaction dynamics of Streptomyces and a bacteriophage in soil.*

Oakley, TH et al, Evolution, vol. 54(2), pp. 397-405, 2000.*

(abstract only), German, Gregory John, Ph.D dissertation, 2003, Receptor interaction and genomic sequence of the ToIC and lipopolysaccharide specific bacteriophage, vol. 64, abstrac 09-6, p. 4186.*

Payne et al, Clinical pharmacology and therapeutics, Sep. 200, pp. 225-230: Phage therapy: The peculier kinetics of self-replicaiting pharmaceuticals.*

Chibani-Chennoufi, S et al, Antimicrobial Agents and Chemotherapy, Jul. 2004, pp. 2558-2569, vol. 48(7).*

Skurnik, Mikael et al, International Journal of Medical Microbiology, vol. 296, pp. 5-14, 2006, Phage Therapy, Facts and fiction.*

Wendlinger, Get al, Microbiology, Apr. 1996, vol. 142(4)pp. 985-992.*

Weld, Richard J., Journal of Theoretical Biology, Vo. 227, pp. 1-11, 2004.*

Bohannan, BJM et al, Ecology Letters, 2000, vol. 3, pp. 362-377.*

Summers, William C, Bacteriophage Therapy, Annu. Rev. Microbiol., 2001, vol. 55, pp. 437-451.*

Tejedor, C et al, Infection and Immunity, Apr. 1982, vol. 36(1), pp. 440-441.*

(Best copy) Souza, KA et al, Journal of Virology, vol. 9(5) pp. 851-856, May 1972.*

Pantucek, Roman et al, Virology, vol. 246, pp. 241-252, 1998.*

Burroughs, NJ et al, App. Environ. Microbiology, Sep. 2000, vol. 66(9), pp. 3868-3877.*

Giese, Michael et al, Am. J. of Ophthalmology, vol. 122(2), pp. 245(10), Aug. 1996.*

Darsavelidze et al., "The Development of a Standard System for the Determination of the Lytic Activity of Pseudomonas-Aeruginosa Bacteriophage," *Izvestiya Akademii Nauk Gruzinskol SSR Seriya Biologicheskaya* 16:330-335 (1990).

Garsevanishvili, "Certain Methodological Aspects of the Use of Inhalation of a Polyvalent Bacteriophage in the Treatment of Pneumonia of Young Children," *Pediatrlia* 53:65-66 (1974).

Seidova et al., "Prevention of Suppuration in Open Fractures," *Vestn. Khir. Im. I. I. Grek.* 117:76-78 (1976).

Ślopek et al., "Results of Bacteriophage Treatment of Suppurative Bacterial Infections. I. General Evaluation of the Results," *Arch. Immunol. Ther. Exp. (Warsz.)* 31:267-291 (1983).

Ślopek et al., "Results of Bacteriophage Treatment of Suppurative Bacterial Infections. II. Detailed Evaluation of the Results," *Arch. Immunol. Ther. Exp. (Warsz.)* 31:293-327 (1983).

Ślopek et al., "Results of Bacteriophage Treatment of Suppurative Bacterial Infections. III. Detailed Evaluation of the Results Obtained in Further 150 Cases," *Arch. Immunol. Ther. Exp. (Warsz.)* 32:317-335 (1984).

Ślopek et al., "Results of Bacteriophage Treatment of Suppurative Bacterial Infections. IV. Evaluation of the Results Obtained in 370 Cases," *Arch. Immunol. Ther. Exp. (Warsz.)* 33:219-240 (1985).

Ślopek et al., "Results of Bacteriophage Treatment of Suppurative Bacterial Infections. V. Evaluation of the Results Obtained in Children," *Arch. Immunol. Ther. Exp. (Warsz.)* 33:241-259 (1985).

Ślopek et al., "Results of Bacteriophage Treatment of Suppurative Bacterial Infections in the Years 1981-1986," *Arch. Immunol. Ther. Exp. (Warsz.)* 35:569-583 (1987).

Sulakvelidze et al., "Bacteriophage Therapy," *Antimicrob. Agents Chemother.* 45:649-659 (2001).

Weber-Dabrowska et al., "Effective Phage Therapy Is Associated with Normalization of Cytokine Production by Blood Cell Cultures," *Arch. Immunol. Ther. Exp. (Warsz.)* 48:31-37 (2000).

Weber-Dabrowska et al., "Bacteriophage Therapy of Bacterial Infections: An Update of Our Institute's Experience," *Arch. Immunol. Ther. Exp. (Warsz.)* 48:547-551 (2000).

* cited by examiner

*Staphylococcus*

845 strains employed in the study of 7 bacteriophages.

Number of Staph. strains $n$ of a new sample for each phage

| Phage no.<br>1-α, d | 1 | 2 | 3 | 4 | 5 | 6 | 7 |
|---|---|---|---|---|---|---|---|
| 0.95, 0.1 | 56 | 24 | 37 | 93 | 93 | 61 | 89 |
| 0.95, 0.05 | 222 | 97 | 149 | 374 | 373 | 245 | 355 |
| 0.95, 10% $p$ | 82 | 28 | 3144 | 535 | 538 | 1548 | 673 |
| 0.98, 0.1 | 66 | 29 | 44 | 111 | 111 | 73 | 106 |

METHODS OF POLYVALENT BACTERIOPHAGE PREPARATION FOR THE TREATMENT OF BACTERIAL INFECTIONS

CROSS REFERENCE TO RELATED APPLICATIONS

This application is the U.S. National Stage of International Application No. PCT/PL02/00053, filed Jul. 18, 2002, which published in English under Article 21(2) PCT and claims priority from Polish Application Nos. P348740 and P354822, each of which is hereby incorporated by reference.

FIELD OF THE INVENTION

The present invention concerns multivalent strains of bacteriophages, methods of obtaining these, and their application in the treatment of bacterial infections, particularly those of drug-resistant strains of bacteria.

BACKGROUND OF THE INVENTION

The bacteriophages (phages) are a diverse group of viruses whose life cycle is connected exclusively with bacteria cells. Bacteriophages are characterized by a lysogenic or lytic life cycle. As anti-bacterial agents, lytic bacteriophages are especially useful which, after infection by bacteria cells to which they are sensitive, they replicate within them, leading to their total destruction (by lysis) and the release of new phages which attack and destroy subsequent bacteria cells. This process may occur both in vitro and in vivo.

One of the essential characteristics of bacteriophages is the well-known high specificity of their lytic activity. This feature is exploited in, for example, species determination (phage typing) of various bacteria (see, for example, patent descriptions GB 2285684, U.S. Pat. No. 5,824,468 and SU 543260, as well as the international patent notifications WO 0100786 and WO 0109370). Other known applications of bacteriophages include their usefulness as tools in molecular biology, for example in the expression and selection of specific proteins (e.g. patent description U.S. Pat. No. 6,027,930), and in sterilization and cleansing media (e.g. patent descriptions EP 0414304, EP 0290295 and GB 2253859, as well as the international patent notifications WO 9808944 and WO 9003122). Modified phages are used in the production of vaccines (e.g. WO 9505454). Certain proteins of bacteriophage origin are also used (e.g. EP 0510907, U.S. Pat. No. 5,470,573, WO 9607329). The methods of isolating bacteriophages and obtaining phage preparations are well known and are constantly being perfected (e.g. GB 829266, CS 192212, RU 2109055).

Phage therapy has been employed on a wide scale since the Second World War at the Institute of Microbiology and Virology of Tbilisi, Georgia. A bank of various phage preparations is used there in the treatment of bacterial infections and in prophylaxis.

Available data indicate a great effectiveness of phage therapy. Similar research has been conducted in Poland for over 25 years. At the Bacteriophage Laboratory of the Institute of Immunology and Experimental Therapy of the Polish Academy of Sciences in Wroclaw the phage therapy is used treatment of infections caused by drug-resistant forms of bacteria and those not susceptible to antibiotics (see: Stefan Ślopek et al., Archivum Immunologiae et Therapiae Experimentalis, 1981, 31, 293; Stefan Ślopek et al., Archivum Immunologiae et Therapiae Experimentalis, 1983, 31, 267; Stefan Ślopek et al., Archivum Immunologiae et Therapiae Experimentalis, 1984, 32, 317; Stefan Ślopek et al., Archivum Immunologiae et Therapiae Experimentalis, 1985, 33, 219; Stefan Ślopek et al., Archivum Immunologiae et Therapiae Experimentalis, 1985, 33, 241; Stefan Ślopek et al., Archivum Immunologiae et Therapiae Experimentalis, 1987, 35, 569; Beata Weber-Dabrowska et al., Archivum Immunologiae et Therapiae Experimentalis, 2000, 48, 31–37; Beata Weber-Dabrowska et al., Archivum Immunologiae et Therapiae Experimentalis, 2000, 48, 547–551). The phage therapy carried out there over the last 14 years, which has included 1473 patients with purulent infections of different tissues and organs, indicates the high efficacy of phage therapy.

Complete abatement of disease symptoms and return to health was noted in 1289 cases. It must be emphasized that in at least a dozen or so cases phage therapy presented the only possibility of eliminating the life-threatening infection. The therapy conducted concerned individual patients. It consisted of:

a) the growth and identification of bacterial strains isolated from material obtained from the patient,
b) determination of the susceptibility of the strain to specific phages and selection of the phage showing the highest lytic activity towards the strain,
c) preparation of a phage lysate with a large number of phage particles,
d) production of a sterile phage preparation for treatment.

This procedure is rather costly, laborious and time consuming. At times, 7–10 days pass from the moment of obtaining the research material to the availability of the finished, sterilized phage preparation for treatment. Such a delay is too long in certain disease states. Phage therapy on a broad scale cannot be carried out with the procedure employed thus far.

Infections accompanying mucoviscidosis present a particular problem. This is a hereditary, systemic disease consisting of dysfunction of mucous-secreting glands, predisposing the patient to chronic bronchial and pulmonary diseases. Secreted mucous is thick and sticky, making its elimination by natural routes (coughing) difficult. The accumulation and lingering of mucous in the bronchi and the impairment in clearing it create favorable conditions for bacterial infections, leading to chronic bronchitis and pneumonia. The most threatening pathogens causing infections accompanying mucoviscidosis are *Staphylococcus aureus* and bacilli of the genus *Pseudonomas*. Permanently recurring infections by these micro-organisms lead to serious pathological changes in the respiratory system and premature death. Few patients survive more than 25 years. Treatment of such infections with the available antibiotics has created a serious therapeutic problem worldwide, especially in the past few years. Antibiotic therapy of these infections has become less and less effective because the vast majority of the bacterial strains show resistance to all antibiotics, including the antibiotic of last resort—vancomycin. There is, therefore, an urgent need to introduce an alternative therapeutic method into medical practice for the treatment of refractory and highly dangerous bacterial infections.

THE GOAL OF THE INVENTION

The past years have seen a massive spread of bacterial strains resistant to all antibiotics, including vancomycin, the antibiotic of last resort. As a result, treatment of bacterial infections induced by these drug-resistant forms with antibiotics is ineffective. This situation has created dramatic therapeutic problems. Thus, there is an urgent need of introducing alternative therapeutic methods into medical practice for the treatment of refractory bacterial infections.

In consideration of the above goal, this invention is an elaboration of a method of obtaining multivalent phage strains which can be used in the production of preparations of guaranteed effectiveness in the treatment of bacterial infections without the necessity of individual phage selection in each instance. In this particular realization, the goal of the invention is the presentation of a way which allows obtaining phage preparations of high purity, in particular free of endotoxin.

A particular goal of the invention is to obtain polyvalent phage preparations which may be effectively employed in the treatment of bacterial infections connected with mucoviscidosis without the necessity of individual phage selection in each instance.

SUMMARY OF THE INVENTION

The present invention provides a method of obtaining multivalent bacteriophage strain, by which:
a) a sufficient number (n) of different strains of bacterial pathogens of a defined genus accumulates, appearing randomly in a given region, whereby the isolated bacterial strains are preferably drug-resistant,
b) a sufficient number of different bacteriophage strains, specific to at least one of the bacterial strains of the given genus, accumulates,
c) the lytic activity of an accumulated bacteriophage strain on each accumulated bacterial strain is determined, then the value p, which is the proportion of the number of strains lysed by a given phage to the number of all the accumulated bacterial strains, is calculated.
d) for the resultant value of p, it is tested whether n fulfils the condition:

$$n \geq \frac{pq}{d^2} z_{1-\alpha}^2$$

where: $q=1-p$
d is a constant no larger than 0.1, optimally no larger that 10% p
$z_{1-\alpha}$ is a random variable of the normal distribution dependent on the confidence factor $1-\alpha$, which is not less that 0.95,
e) the bacteriophage strain is selected which fulfils the criterion defined in d) and has a value of p not less than 2/n, preferably not less than 0.5.

The range of the lytic activity of each isolated bacteriophage is determined with regard to the population of pathogenic bacterial strains present in the given region. To this end, a sufficiently large collection of randomly chosen drug-resistant bacterial strains must be accumulated. With reference to the established large sample of bacteria of a population size of n strains (in the example described, n was 845 and 880, respectively, for the drug-resistant strains of *Pseudomonas* and *Staphylococcus* isolated in Poland), the frequency of success is calculated, or the proportion of the number of strains lysed by a given phage to the total number of strains studied. This frequency is regarded as the probability of success p. The probability of failure is then $q=1-p$.

It is essential to choose the size n that a sample must have so that it can be regarded as representative of the general population of the strains of the given genus (e.g. *Pseudomonas* or *Staphylococcus*). To this end, the following criterion for the sample to be representative is established:

$$P(|v-p|<d)=P(-d<v-p<d)=1-\alpha$$

The probability that the absolute value of the difference between the sample frequency v and the probability of success p is less than the pre-assigned value of d is $1-\alpha$, which corresponds with a confidence level of $1-\alpha$. The value of $1-\alpha$ is usually set at 0.95 or 0.98.

The number of samples n should fulfil the condition:

$$n \geq \frac{pq}{d^2} z_{1-\alpha}^2$$

where $z_{1-\alpha}$ is a random variable of the normal distribution. For $1-\alpha=0.95$, $z_{1-\alpha}=1.96$, and for $1-\alpha=0.98$, $z_{1-\alpha}=2.33$.

Based on this criterion and on the value of the frequency p obtained for the characterized phage, by assigning reasonable values to d and the confidence range $1-\alpha$ it is possible to verify the magnitude n used to determine the range of lytic activity of a given phage and ascertain whether the lytic activity obtained for this n, with the assigned values of d and $1-\alpha$, may be regarded as correct with respect to the general population of the bacterial strains of the given genus.

The strain of bacteriophages is preferably isolated in step b) from a sample originating from the environment by passing it through a membrane filter of pore size 0.2–0.4 µm, adding culture medium to the filtrate and mixing it with a broth culture of bacteria of the defined genus, incubating this at a temperature of about 37° C. for approximately one hour, removing a portion of the suspension and smearing it onto plates with solid culture medium, incubating at approx. 37° C. for 2 to 24 hours, isolating a sample of the medium surrounding the individual bald spot, transferring it to the broth culture of bacteria of defined genus, and incubating until the culture clears, and obtaining the bacteriophage preparation by passing the lysate through a membrane filter of pore size 0.2–0.4 µm, whereby it is preferred to repeat the inoculation of the solid culture medium and re-isolation of the bald spots 5 times.

The bacterial strains in step c) are preferably inoculated onto solid culture medium, onto which a portion of the bacteriophage preparation obtained in step b) is deposited, incubated at about 37° C. for around 4 hours, after which the temperature is set at about 4° C. for around 2 to 24 hours, by which the lytic activity of the bacteriophage strain is evidenced by the appearance of, at least, individual bald spots.

It is possibly to carry out then further purification of the lysate, particularly with regard to endotoxin, whereby the mixture containing bacteriophages is in contact with a substrate containing cellulose or a partially esterified derivative of it, then rinsed with a solution that removes impurities, especially endotoxin, after which the purified bacteriophages are washed out. The endotoxin can be effectively eluted with water, a solution of a non-dissociating substance, or a saline solution of concentration no greater than 0.1 M, possibly buffered. The bacteriophage fraction can also be effectively eluted with a solution of a non-dissociating substance, or any buffer, or a saline solution of concentration greater than 0.05 M, possibly buffered. Also, elution of endotoxin and bacteriophages are carried out at temperatures between $-25°$ C. and $+100°$ C. Preferably, the endotoxin and bacteriophage elution can be done using an aqueous saline solution containing organic solvent. The organic solvent is best selected from a group comprising dimethyl sulphoxide, dimethylformamide, isopropanol and acetone, and as a substrate cellulose partially esterified with organic or inorganic acid can be used. It may be used a substrate of cellulose partially esterified with acetic, nitric, sulphurous or phosphoric acid, in particular cellulose may be used as a substrate of which 0.01 to 5% of the glucose molecules have been esterified, preferably 0.25 to 1%, more preferably from 0.5 to 1% of the glucose molecules.

Preferably the pathogenic bacterial strains are of the genera *Staphylococcus* or *Pseudomonas*.

A further aspect of the invention is a medication for the treatment or prevention of infections caused by bacterial pathogens which contains an active agent and a possible pharmaceutically admissible carrier, such that the active agent is comprised of a multivalent bacteriophage strain specific to the bacteria of the genus and obtained using the method of this invention.

In accordance with the invention, the medication may have the characteristic that, as a multivalent bacteriophage strain specific to bacteria of the genus *Staphylococcus*, it contains at least one strain of bacteriophages selected from among S1 (PCM F/00001), S2 (PCM F/00002), S3 (PCM F/00003), S4 (PCM F/00004), S5 (PCM F/00006), S6 (PCM F/00006) and S7 (PCM F/00007), preferably the phages S1, S2, and S4 or S5. This medication produced in accordance with the one aspect of the invention is to serve in the treatment or prevention of infections arising in persons afflicted with mucoviscidosis and, as a multivalent bacteriophage strain specific to bacteria of the genus *Staphylococcus*, it contains at least one bacteriophage strain selected from among F/00002, F/00004 and F/00007.

In accordance with the invention, the medication should have the characteristic that, as a multivalent bacteriophage strain specific to bacteria of the genus *Pseudomonas*, it contains at least one strain of bacteriophages selected from among P1 (PCM F/00008), P2 (PCM F/00009), P3 (PCM F/00010), P4 (PCM F/00011), P5 (PCM F/00012), P6 (CM F/00013), P7 (PCM F/00014), P8 (CM F/00015), P9 (PCM F/00016), P10 (PCM F/00017), P11 (PCM F/00018), P12 (PCM F/00019), P13 (PCM F/00020), P14 (PCM F/00021), P15 (PCM F/00022), P16 (PCM F/00023), P17 (PCM F/00024), P18 (PCM F/00025), P19 (PCM F/00026), and P20 (PCM F/00027), optimally phages P7, P20 and P6. The medication produced in accordance with certain aspect of the invention is to serve in the treatment or prevention of infections arising in persons afflicted with mucoviscidosis and, as a multivalent bacteriophage strain specific to bacteria of the genus *Pseudomonas*, it contains at least one bacteriophage strain selected from among F/00010, F/00013 and F/00018.

A further object of this invention is the application of a multivalent bacteriophage strain obtained according to the method of the invention to the development of a medication for the treatment or prevention of bacterial infections caused by bacterial pathogens.

Advantageous for the production of a medication for the treatment or prevention of infections caused by bacteria of the genus *Staphylococcus* is the employment of at least one bacteriophage strain selected from among S1 (PCM F/00001), S2 (PCM F/00002), S3 (PCM F/00003), S4 (PCM F/00004), S5 (PCM F/00006), S6 (PCM F/00006) and S7 (PCM F/00007), optimally phages S1, S2, and S4 or S5. Advantageous for the creation of a medication for the treatment or prevention of infections caused by bacteria of the genus *Staphylococcus* in persons suffering from mucoviscidosis is the use of at least one bacteriophage strain chosen from among F/00002, F/00004 and F/00007.

Also advantageous for the creation of a medication for the treatment or prevention of infections caused by bacteria of the genus *Pseudomonas* is the use of at least one bacteriophage strain selected from among P1 (PCM P/00008), P2 (PCM F/00009), P3 (PCM F/00010), P4 (PCM F/00011), P5 (PCM F/00012), P6 (PCM F/00013), P7 (PCM F/00014), P8 (PCM F/00015), P9 (PCM F/00016), P10 (PCM F/00017), P11 (PCM F/00018), P12 (PCM F/00019), P13 (PCM F/00020), P14 (PCM F/00021), P15 (PCM F/00022), P16 (PCM F/00023), P17 (PCM F/00024), P18 (PCM F/00025), P19 (PCM F/00026), and P20 (PCM F/00027), optimally the phages P7, P20 and P6. Advantageous for the creation of a medication for the treatment or prevention of infections caused by bacteria of the genus *Pseudomonas* in persons suffering from mucoviscidosis is the use of at least one bacteriophage strain chosen from among F/00010, F/00013 and F/00018.

A further object of the invention is a multivalent bacteriophage strain specific to bacteria of the genus *Staphylococcus* selected from among S1 (PCM F/00001), S2 (PCM F/00002), S3 (PCM F/00003), S4 (PCM F/00004), S5 (PCM F/00006), S6 (PCM F/00006) and S7 (PCM F/00007), optimally from among S1, S2, S4 and S5.

An object of the invention is also a multivalent bacteriophage strain specific to bacteria of the genus *Pseudomonas*, selected from among P1 (PCM F/00008), P2 (PCM F/00009), P3 (PCM F/00010), P4 (PCM F/00011), P5 (PCM F/00012), P6 (PCM F/00013), P7 (PCM F/00014), P8 (PCM F/00015), P9 (PCM F/00016), P10 (PCM F/00017), P11 (PCM F/00018), P12 (PCM F/00019), P13 (PCM F/00020), P14 (PCM F/00021), P15 (PCM P/00022), P16 (PCM F/00023), P17 (PCM F/00024), P18 (PCM F/00025), P19 (PCM F/00026), and P20 (PCM F/00027), optimally from among P7, P20 and P6.

Our own collection of phages active against species of bacteria which are the most frequent etiologic factors in bacterial infection in humans was used in the research. The practical examples described concern multivalent bacteriophages acting lytically on strains of staphylococci (*Staphylococcus aureus*), including the methicillin-resistant strains thereof, and the blue pus bacillus (*Pseudomonas aeruginosa*), which appear in those afflicted with mucoviscidosis in particular. These species are currently the cause of serious infections causing high mortality.

THE VIRTUES OF THE INVENTION

The introduction into therapy of polyvalent phage preparations containing multivalent phages obtained by means of this invention is a major development in combating bacterial infections which are not susceptible to treatment with antibiotics. Certain economic advantages are also connected with this new technology. It allows a significant reduction in material costs and shortens the time from collecting material for examination to obtaining the therapeutic phage preparation. Thanks to this, the phage preparation will wait for the patient, and not the patient for the production of the individual phage preparation.

The broad range of lytic phage preparations composed of several multivalent phages obtained by means of the method of this invention is a very important advantage from the viewpoint of their application in the treatment of bacterial infections. It is well known that within a bacterial population, forms resistant to a bacteriophage can appear with a frequency of about $1\times10^{-7}$. In the presence of two phages, the frequency of such mutation is about $1\times10^{-14}$, and with three phages only $1\times10^{-21}$. With such an arrangement, the problem of bacterial strain resistance to phages practically does not exist.

The great applicability of the exemplified medications composed of multivalent phages deserves special emphasis. They may be employed in the medical practice in general and allow an effective means of coping with threatening bacterial infections. It is also possible to exploit phages obtained in accordance with this invention in the preparation of medications for external use, employing them, for example, in the treatment and prevention of dermatological infections. It has been found that oral administration of phage lysates obtained according to this invention increases resistance to possible future bacterial infection.

In certain cases, phage therapy can be used in conjunction with antibiotic therapy. Polyvalent phage preparations used in the treatment of bacterial infections have been show to be highly effective. Particular effectiveness has been observed in the treatment of sepsis (88% cure rate) and in the treatment of infections in patients with mucoviscidosis.

Figure 1:
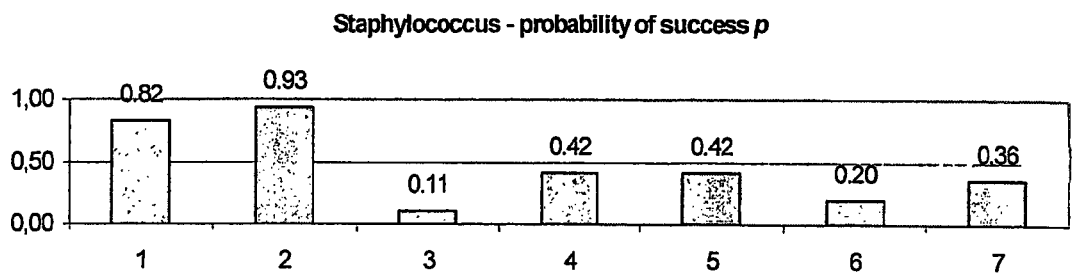
FIG. 1 presents the results of the analysis of statistics acquired for phages S1–S7.

For a better understanding of the essence of the invention, it is illustrated below through examples.

EXAMPLE 1

Bacteriophage Isolation

Bacteriophages for *Staphylococcus* and *Pseudomonas* were isolated from municipal sewage. The sewage was passed through a membrane filter with a pore size of 0.2–0.4 μm, which captures the bacteria but allows the bacteriophages to pass through. From the resultant filtrate, concentrated fluid culture medium was added and different dilutions of filtrate were mixed with young broth cultures of bacteria (*Staphylococcus aureus* or *Pseudomonas aeruginosa*). The samples were incubated at 37° C. for 1 hour, after which 0.2 ml of suspension was extracted from each sample with a pipette and smeared onto plates containing agar medium using a glass rod and the plates were incubated overnight at 37° C. In the event that the sought after phage was present on the plates inoculated with the suitable dilution of filtrate containing the young bacterial culture, a uniform (nebulous) growth of bacteria and separate, transparent small fields, the so-called bald spots, were observed, which usually contained several million phage particles. The individual bald spot together with the agar surrounding it were cut out with the aid of a platinum loop, then transferred to a fresh broth culture of bacteria and incubated until the culture cleared. After passing it through a membrane filter of pore size 0.2–0.4 μm, which holds back any bacteria remaining in the lysate, the filtrate contained only bacteriophages. The inoculation of different dilutions of the obtained phages with the respective bacteria on agar medium, and the re-isolation of the bald spots was carried out 5 times, which allowed obtaining a pure line of phages.

EXAMPLE 2

Determining the Susceptibility of *Staphylococcus aureus* Strains to Bacteriophage Microorganisms Specific to them Susceptibility was determined using the culture medium described by Wahl. Plates with this medium were dried at a temperature of 37° C. for 30 minutes, covered with a young, 4-hour broth culture of *Staphylococcus aureus* which was mixed by shaking, the excess of the suspension was removed with a pipette and again dried for 30 minutes at 37° C. On one plate, divided into 6 segments, the susceptibilities of the strain under study was determined to 6 different but specific bacteriophages. One drop of a 1/10 bacteriophage dilution was placed onto the surface of each segment. The plates were incubated in an oven at 37° C. for about 4 hours, after which they were placed in a refrigerator until the following day. In the event of a high susceptibility of the strain to the defined phage, transparent fields are visible at the place where the phage was introduced onto the culture medium which was uniformly covered with bacterial growth, these being the result of the total destruction of bacteria cells (lysis). Less susceptibility of the strain is manifested by the appearance of individual bald spots.

EXAMPLE 3

Determining the Susceptibility of Strains of *Pseudomonas* to Bacteriophage Microorganisms Specific to them The method of determining the sensitivity was similar to that described in Example 2. In this case, though, the stock medium was agar with a phosphate buffer supplement and the incubation time of the plates deposited phage was 5 hours.

EXAMPLE 4

Selecting Phages with the Broadest Spectrum of Activity with Regard to *Staphylococcus* and *Pseudomonas* Strains—Obtaining Multivalent Phage Strains Bacteriophages were isolated according to the method described in Example 1. The susceptibilities of 845 drug-resistant clinical strains of various species of *Staphylococcus* isolated from all over Poland to phages from the collection of bacteriophages specific to *Staphylococcus*, and the susceptibilities of 880 drug-resistant clinical strains of different species of *Pseudomonas* to phages from the collection of bacteriophages specific to *Pseudomonas* were determined.

An analysis of the susceptibilities of both groups of strains to the respective phages allowed the selection of phages of unexpectedly high activity and broad spectrum of lytic effect. These phages are presented in tables 1 and 2.

TABLE 1

Phages for *Staphylococcus* with high lytic activity on deposit at the Polish Collection of Microorganisms (PCM), Wroclaw, Poland.

| PHAGE DESIGNATION | POLISH COLLECTION OF MICROORGANISMS (PCM) DEPOSIT ACCESS NUMBER |
| --- | --- |
| S1 | F/00001 |
| S2 | F/00002 |
| S3 | F/00003 |
| S4 | F/00004 |
| S5 | F/00005 |
| S6 | F/00006 |
| S7 | F/00007 |

TABLE 2

Phages for *Pseudomonas* with high lytic activity on deposit at the Polish Collection of Microorganisms (PCM), Wroclaw, Poland.

| PHAGE DESIGNATION | POLISH COLLECTION OF MICROORGANISMS (PCM) DEPOSIT ACCESS NUMBER |
| --- | --- |
| P1 | F/00008 |
| P2 | F/00009 |
| P3 | F/00010 |
| P4 | F/00011 |
| P5 | F/00012 |
| P6 | F/00013 |
| P7 | F/00014 |
| P8 | F/00015 |
| P9 | F/00016 |
| P10 | F/00017 |
| P11 | F/00018 |
| P12 | F/00019 |

TABLE 2-continued

Phages for *Pseudomonas* with high lytic activity on deposit at the Polish Collection of Microorganisms (PCM), Wroclaw, Poland.

| PHAGE DESIGNATION | POLISH COLLECTION OF MICROORGANISMS (PCM) DEPOSIT ACCESS NUMBER |
| --- | --- |
| P13 | F/00020 |
| P14 | F/00021 |
| P15 | F/00022 |
| P16 | F/00023 |
| P17 | F/00024 |
| P18 | F/00025 |
| P19 | F/00026 |
| P20 | F/00027 |

Figure 2:
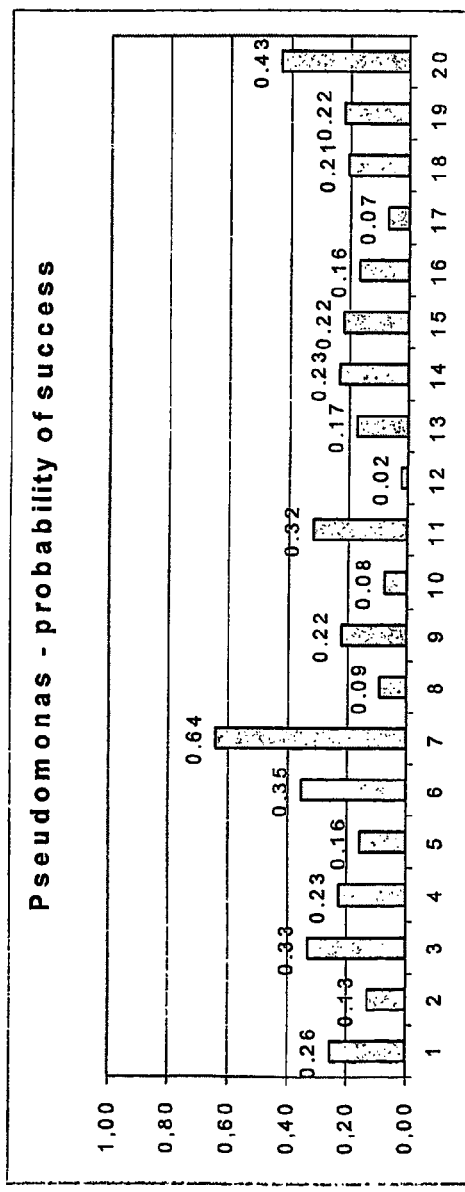
FIG. 2 presents the results of the analysis of statistics acquired for phages P1–P20.

The results for phages S1–S7 and P1–P20 were submitted to statistical analysis in order to determine whether the p values obtained for the particular phages may be considered correct for the general populations of the respective genera of bacteria. The results are presented in FIGS. 1 and 2. The calculated values of n for most of the bacteriophages were lower than the number of bacterial strains of the research samples, which suggests that the ranges of the lytic spectra are at least correct with regard to the clinical strains appearing in Poland. Considering these results, the phages listed in Tables 1 and 2 may be regarded as multivalent phages with regard to this invention.

Unexpectedly, in the case of the phages for *Staphylococcus*, 3 of the 7 most active, i.e. S1, S2 and S4 or S5, displayed lytic activity on 95% of the *Staphylococus* strains studied. Also, 3 of the 21 selected phages for *Pseudomonas*, i.e. P7, P20 and P6, displayed lytic activity on 87% of the *Pseudomonas* strains studied.

Figure 3:
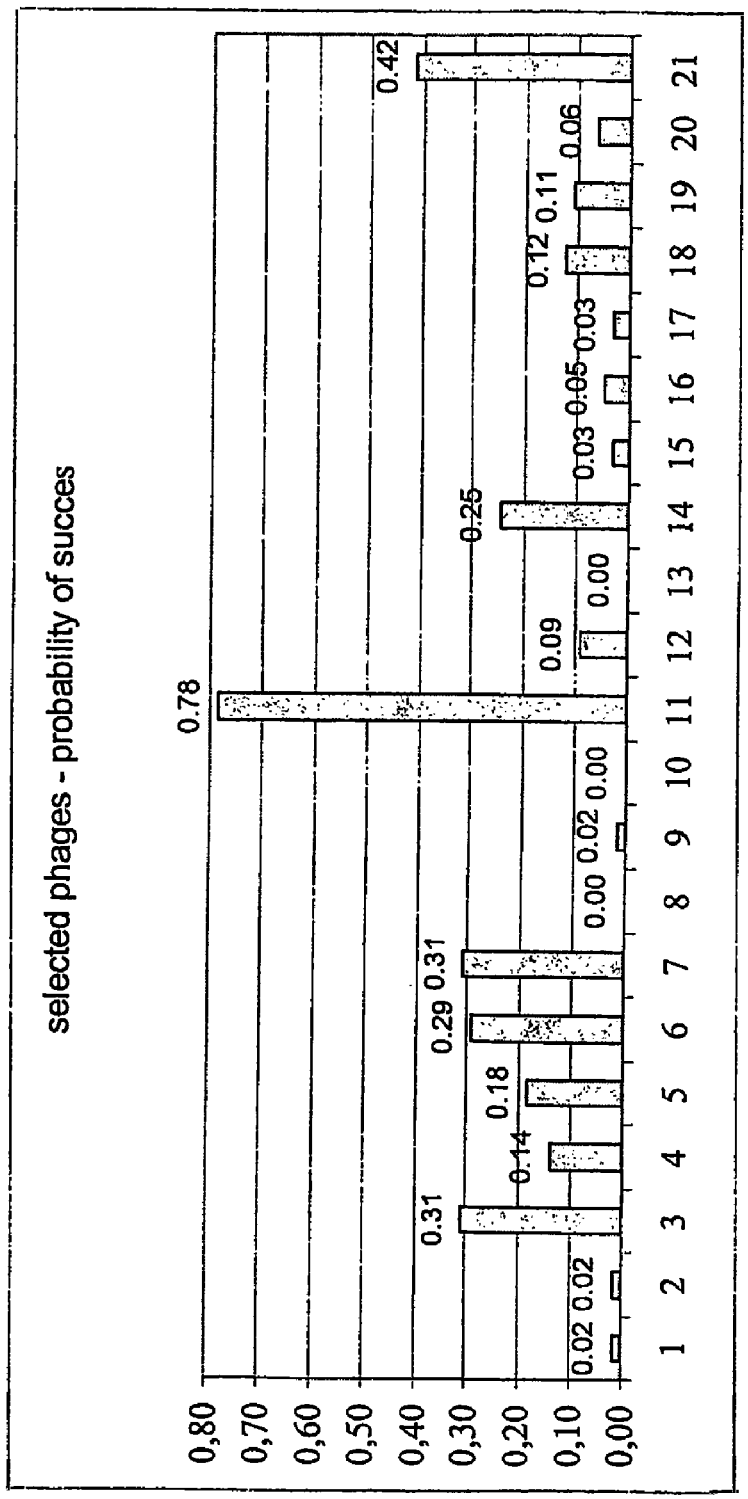
FIG. 3 presents the results of the statistical analysis of the effectiveness of selected phage strains with regard to bacterial strains belonging to the genus *Staphylococcus* isolated from mucoviscidosis patients.
Figure 4:
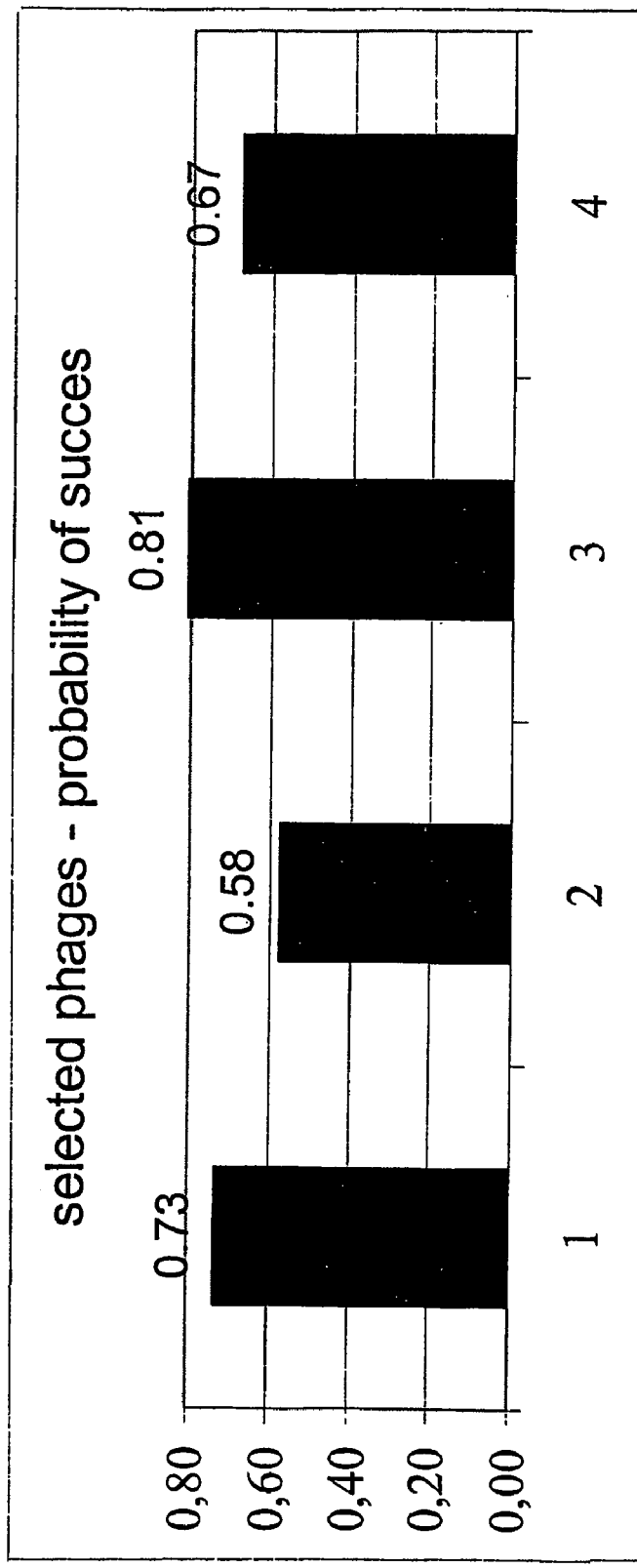
FIG. 4 presents the results of the statistical analysis of the effectiveness of selected phage strains with regard to bacterial strains belonging to the genus *Pseudomonas* isolated from mucoviscidosis patients.

One may also regard patients suffering from mucoviscidosis as a "given region of the appearance of bacterial infection", as defined in the essence of the invention. In the study of the pathogens appearing in this group of patients, 137 bacterial strains were used, of which 84 were identified as *Pseudomonas* and 53 as *S. aureus*. All the strains were isolated from material originating from mucoviscidosis patients from all over Poland. Analysis of the susceptibility of the strains of *Pseudomonas* and *S. aureus* studied to phages allowed the selection of phages with the highest lytic activity and the broadest range of action. Unexpectedly, in the case of phages for *Pseudomonas*, 3 of the 21 active phages, i.e. F/00010, F/0013 and F/00018, displayed lytic activity on 75% of the *Pseudomonas* strains (for the probability of success, see FIG. 3, in which phage 3=F/00010, phage 6=F/00013, and phage 11=F/00018). Among the selected phages for *Staphylococcus*, 3, i.e. F/00002, F/00004 and F/00007, displayed lytic activity on 98% of the *Staphylococcus* strains (for the probability of success, see FIG. 4, in which phage 1=F/00002, phage 3=F/00004, and phage 4=F/00007).

EXAMPLE 5

Replicating Phages to *Staphylococcus* and Phages to Gram-Negative Bacilli, Obtaining Phage Lysates Approximately 5% phage lysate was added to young, 4-hour cultures of *Staphylococcus aureus* (logarithmic phase) in broth medium supplemented by glucose. The test tubes or bottles were mixed by shaking and incubated for 3 hours at 37° C. After the appearance of a clear culture (lysis), the samples were kept cold until the following day. The lysate was passed through a membrane filter of pore size 0.2–04 µm to remove any remaining unlysed bacteria cells. The concentration of live phage particles was determined by the two-layer method of Gratia. An incubated culture without the addition of phage lysate served as a control.

Replicating phages to Gram-negative bacilli (*Pseudomonas*). Peptone water was used to replicate phages to *Pseudomonas*. 5% phage lysate was added to a young, 4-hour culture of *Pseudomonas aeurginosa*, the test tubes or bottles were mixed by shaking and the samples were incubated for 5 hours at 37° C. After the culture had cleared up, the samples were left until the following day in a refrigerator, after which they were filtered through a membrane filter with pore size as above. The number of live phage particles in the lysate was determined by the method of Gratia.

The sterile broth phage lysates show long-lasting lytic activity. When kept cold, they maintain their vitality for several years, in some cases over 10 years.

EXAMPLE 6

The Production and Application of Polyvalent Phage Preparations

The sterile broth lysate obtained by the method described in Example 5, originating from the phages selected with a broad spectrum of lytic activity in Example 4, or their concentrated or further purified forms (see the following example), served in the preparation of polyvalent phage medications.

The exemplified polyvalent phage preparation to *Staphylococcus* is a mixture containing different amounts of the lysates of phages S1, S2 and S4 or S5, or derivatives of these lysates. For infections arising from *Staphylococcus* in mucoviscidosis patients, preparations from phages F/00002, F/00004 and F/00007 should be used.

The exemplified polyvalent phage preparation to *Pseudomonas* is a mixture containing different amounts of the lysates of phages P7, P20 and P6, or derivatives of these lysates. For infections arising from *Pseudomonas* in mucoviscidosis patients, preparations from phages F/00010, F/00013 and F/00018 should be used.

The medication is administered orally 3 times daily, in quantities corresponding to 10 ml of lysate, 30 minutes before meals, after previous neutralization of stomach fluids (e.g. with Gel Alumini phosphorici, purified soda or VIchy water). When applying the preparation directly onto wounds, it should be done 3 times over 24 hours. By local application, the wound should not be cleansed with disinfectant, as this may lead to inactivation of the phages. If necessary, wounds may be cleansed with a sterile culture medium or a 0.9% NaCl physiological solution.

In certain cases, phage therapy may be employed in conjunction with antibiotic therapy. The polyvalent phage preparations used in the treatment of bacterial infections have displayed high effectiveness. Particular efficacy has been observed in the treatment of sepsis (88% cure rate) and infections arising in mucoviscidosis patients.

EXAMPLE 7

Further Purification of Bacteriophage Preparations, Removing Endotoxin from Mixtures Containing Bacteriophages In several medical applications, or also due to methods of administration (e.g. intravenously), bacteriophage preparations of high purity are required, in particular that they be devoid of bacterial endotoxin. Following the method of this invention, the affinity of bacteriophages to a substrate containing cellulose or, optimally, an esterified derivative of it, was used. A commercially available sulphated derivative of cellulose was used in this example, which was characterized by a low level of esterification (8 µmole/ml of gel). The substrate was used to remove endotoxin from the mixture containing bacteriophages. After rinsing the substrate and removing the endotoxin, the next step of purification is the elution of the adsorbed bacteriophages.

One ml of substrate containing the sulphated derivative of cellulose was put into the sterile column of a chromatograph. Efflux of the substrate from the column was prevented by sealing the lower part of the column with glass wool soaked with 70% ethanol.

The following elution buffers were prepared:

Buffer I: 0.01 M phosphate buffer, pH 7.6;

Buffer II: 0.01 M phosphate buffer, pH 7.6, containing 1 M sodium chloride.

The salts entering into the composition of the eluent were baked for 1 hour at 145° C.

The solutions were prepared using distilled apyrogenic water.

Before chromatography, 1 ml of substrate was filled into a chromatograph column rinsed with 5 ml of buffer I, and then 5 ml of buffer II.

The column was prepared for the actual chromatography by rinsing it with 10 ml buffer I.

Removal of endotoxin was accomplished by using the large-molecule fraction obtained in the molecular sieve procedure on Sepharose 4B of the concentrated bacteriophage lysate Ps PCM F/00018.

0.2 ml of the bacteriophage mixture was transferred to a chromatograph column containing 1 ml substrate containing the sulphated derivative of cellulose. A fraction of 0.2 ml volume was taken. The first fraction was eluted with 3 ml of buffer I. Under these conditions, non-associated endotoxin flowed out from the column. The second fraction was eluted with buffer II. Fraction II contained purified bacteriophages.

The results of units of endotoxin in the fractions:

The material submitted to chromatography on a substrate containing a sulphated derivative of cellulose contained 2500 units of endotoxin/ml. The fraction eluted with buffor I contained 600–1000 units of endotoxin/ml, and that eluted with buffer II contained bacteriophages devoid of endotoxin (about 1 unit/ml).

The content of endotoxin in the bacteriophage preparations was determined using the gel method of the company Charles River Endosafe, Charleston, USA.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCLAW, POLAND<br><br>NAME AND ADDRESS OF DEPOSITOR | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |

| I. IDENTIFICATION OF THE MICROORGANISM | |
|---|---|
| Identification reference given by the DEPOSITOR:<br><br>S1 | Accession number given by the INTERNATIONAL DEPOSITARY AUTHORITY:<br><br>F/00001 |
| II. SCIENTIFIC DESCRIPTION AND/OR PROPOSED TAXONOMIC DESIGNATION | |
| The microorganism identified under I above was accompanied by:<br><br>☐ a scientific description<br><br>☒ a proposed taxonomic designation  Siphoviridae SI19<br>(Mark with a cross where applicable) | |
| III. RECEIPT AND ACCEPTANCE | |
| This International Depositary Authority accepts the microorganism identified under I above, which was received by it on (date of the original deposit)¹ 18.07.2001 | |
| IV. INTERNATIONAL DEPOSITARY AUTHORITY | |
| Name: Polish Collection of Microorganisms<br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18.09.2001 |

¹ Where Rule 6.4.(d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00001<br>Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR: S2 | Accession number given by the INTERNATIONAL DEPOSITARY AUTHORITY: F/00002 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation   Siphoviridae SI9<br>(Mark with a cross where applicable) |

| III. RECEIPT AND ACCEPTANCE |
|---|
| This International Depositary Authority accepts the microorganism identified under I above, which was received by it on (date of the original deposit)[1]   18.07.2001 |

| IV. INTERNATIONAL DEPOSITARY AUTHORITY | |
|---|---|
| Name: Polosh Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):<br><br>Date: |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF THE PARTY TO WHOM THE VIABILITY STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00002<br>Date of the deposit or of the transfer:<br>18.07.2001 |

III. VIABILITY STATEMENT

The viability of the microorganism identified under II above was tested on 1.09.2001 [2]. On that date, the said microorganism was

[X][3] viable

[ ][3] no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: Polish Collection of Microorganisms<br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>S3 | Accession number given by the INTERNATIONAL DEPOSITARY AUTHORITY:<br><br>F/00003 |

| II. SCIENTIFIC DESCRIPTION AND/OR PROPOSED TAXONOMIC DESIGNATION |
|---|
| The microorganism identified under I above was accompanied by:<br><br>[ ] a scientific description<br><br>[X] a proposed taxonomic designation  Siphoviridae SI19<br>(Mark with a cross where applicable) |

| III. RECEIPT AND ACCEPTANCE |
|---|
| This International Depositary Authority accepts the microorganism identified under I above, which was received by it on (date of the original deposit)¹  18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):<br><br>Date: 18.09.2001 |

¹ Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF THE PARTY TO WHOM THE VIABILITY STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00003<br>Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X] [3] viable<br><br>[ ] [3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| | |
| V. INTERNATIONAL DEPOSITARY AUTHORITY | |
| Name: Polish Collection of Microorganisms<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001  |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|---|

| I. IDENTIFICATION OF THE MICROORGANISM | |
|---|---|
| Identification reference given by the DEPOSITOR: <br><br> S4 | Accession number given by the INTERNATIONAL DEPOSITARY AUTHORITY: <br><br> F/00004 |
| II. SCIENTIFIC DESCRIPTION AND/OR PROPOSED TAXONOMIC DESIGNATION | |
| The microorganism identified under I above was accompanied by: <br><br> ☐ a scientific description <br><br> ☒ a proposed taxonomic designation    Siphoviridae SI10 <br> (Mark with a cross where applicable) | |
| III. RECEIPT AND ACCEPTANCE | |
| This International Depositary Authority accepts the microorganism identified under I above, which was received by it on (date of the original deposit)[1]  18.07.2001 | |
| IV. INTERNATIONAL DEPOSITARY AUTHORITY | |
| Name: Polish Collection of Microorganisms <br> Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s): <br><br> Date: 19.07.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO<br><br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF<br>THE PARTY TO WHOM THE VIABILITY<br>STATEMENT IS ISSUED | VIABILITY STATEMENT<br>issued pursuant to Rule 10.2 by the<br>INTERNATIONAL DEPOSITARY AUTHORITY<br>identified on the following page |
|---|---|

| I. DEPOSITOR | II. IDENTIFICATION OF THE MICROORGANISM |
|---|---|
| Name:  LUDWIK HIRSZFELD INSTITUTE<br>OF IMMUNOLOGY AND EXPERIMENTAL THERAPY<br>Polish Academy of Sciences<br>Address: Rudolfa Weigla 12, 53-114 WROCŁAW, POLAND | Accession number given by the<br>POLISH COLLECTION OF MICROORGANISMS<br>F/00004<br>Date of the deposit or of the transfer:<br>18.07.2001 |

| III. VIABILITY STATEMENT |
|---|
| The viability of the microorganism identified under II above was tested on 1.09.2001 [1]. On that date, the said microorganism was [2]<br><br>[X] [3] viable<br><br>[ ] [3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganisms<br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09, 2001 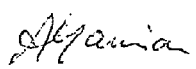 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>S5 | Accession number given by the INTERNATIONAL DEPOSITARY AUTHORITY:<br><br>F/00005 |

| II. SCIENTIFIC DESCRIPTION AND/OR PROPOSED TAXONOMIC DESIGNATION |
|---|
| The microorganism identified under I above was accompanied by:<br><br>☐    a scientific description<br><br>☒    a proposed taxonomic designation    siphoviridae SI19<br>(Mark with a cross where applicable) |

| III. RECEIPT AND ACCEPTANCE |
|---|
| This International Depositary Authority accepts the microorganism identified under I above, which was received by it on (date of the original deposit)[1] 18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF THE PARTY TO WHOM THE VIABILITY STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Address: Rudolfa Weigla 12, 53-114 WROCŁAW, POLAND | Accession number given by the POLISH COLLECTION OF MICROORGANISMS F/00005 Date of the deposit or of the transfer: 18.07.2001 |

III. VIABILITY STATEMENT

The viability of the microorganism identified under II above was tested
on  1.09.2001  [2]. On that date, the said microorganism was

[X] [3]  viable

[ ] [3]  no longer viable

---

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| V. INTERNATIONAL DEPOSITARY AUTHORITY | |
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s): <br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>S6 | Accession number given by the INTERNATIONAL DEPOSITARY AUTHORITY:<br><br>F/00006 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation Siphoviridae SI19<br>(Mark with a cross where applicable) |

| III. RECEIPT AND ACCEPTANCE |
|---|
| This International Depositary Authority accepts the microorganism identified under I above, which was received by it on (date of the original deposit)[1]    18.07.2001 |

| IV. INTERNATIONAL DEPOSITARY AUTHORITY | |
|---|---|
| Name: Polish Collection of Microorganisms<br>LUDWIK HIRSZFELD INSTITUTE<br>Address: OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND Address: | Accession number given by the POLISH COLLECTION OF MICROORGANISMS F/00006 Date of the deposit or of the transfer: 18.07.2001 |

III. VIABILITY STATEMENT

The viability of the microorganism identified under II above was tested
on    1.09.2001                        [2]. On that date, the said microorganism was

[X][3]   viable

[ ][3]   no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18, 09, 2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|---|

| I. IDENTIFICATION OF THE MICROORGANISM | |
|---|---|
| Identification reference given by the DEPOSITOR: S7 | Accession number given by the INTERNATIONAL DEPOSITARY AUTHORITY: F/00007 |

| II. SCIENTIFIC DESCRIPTION AND/OR PROPOSED TAXONOMIC DESIGNATION |
|---|
| The microorganism identified under I above was accompanied by: |
| ☐ a scientific description |
| ☒ a proposed taxonomic designation  Siphoviridae SI19 |
| (Mark with a cross where applicable) |

| III. RECEIPT AND ACCEPTANCE |
|---|
| This International Depositary Authority accepts the microorganism identified under I above, which was received by it on (date of the original deposit)¹  18.07.2001 |

| IV. INTERNATIONAL DEPOSITARY AUTHORITY | |
|---|---|
| Name: Polish Collection of Microorganisms  Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):  Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND  NAME AND ADDRESS OF THE PARTY TO WHOM THE VIABILITY STATEMENT IS ISSUED | VIABILITY STATEMENT issued pursuant to Rule 10.2 by the INTERNATIONAL DEPOSITARY AUTHORITY identified on the following page |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Address: Rudolfa Weigla 12, 53-114 WROCŁAW, POLAND | Accession number given by the POLISH COLLECTION OF MICROORGANISMS F/00007 Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X][3]  viable<br><br>[ ][3]  no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
| --- |
| |

| V. INTERNATIONAL DEPOSITARY AUTHORITY | |
| --- | --- |
| Name: Polish Collection of Microorganisms<br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09. 2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12 53-114 WROCLAW, POLAND | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|---|
| | NAME AND ADDRESS OF DEPOSITOR | |

| I. IDENTIFICATION OF THE MICROORGANISM ||
|---|---|
| Identification reference given by the DEPOSITOR:<br><br>P1 | Accession number given by the INTERNATIONAL DEPOSITARY AUTHORITY:<br><br>F/00008 |
| II. SCIENTIFIC DESCRIPTION AND/OR PROPOSED TAXONOMIC DESIGNATION ||
| The microorganism identified under I above was accompanied by:<br><br>☐ a scientific description<br><br>[X] a proposed taxonomic designation   Myoviridae M11<br>(Mark with a cross where applicable) ||
| III. RECEIPT AND ACCEPTANCE ||
| This International Depositary Authority accepts the microorganism identified under I above, which was received by it on (date of the original deposit)[1]    18.07.2001 ||
| IV. INTERNATIONAL DEPOSITARY AUTHORITY ||
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF THE PARTY TO WHOM THE VIABILITY STATEMENT IS ISSUED | VIABILITY STATEMENT<br>issued pursuant to Rule 10.2 by the<br>INTERNATIONAL DEPOSITARY AUTHORITY<br>identified on the following page |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY<br>Polish Academy of Sciences<br>Address: Rudolfa Weigla 12, 53-114 WROCŁAW, POLAND | Accession number given by the<br>POLISH COLLECTION OF MICROORGANISMS<br>F/00008<br>Date of the deposit or of the transfer:<br>18.07.2001 |

III. VIABILITY STATEMENT

The viability of the microorganism identified under II above was tested
on           1.09.2001           [2]. On that date, the said microorganism was

[X][3]   viable

[ ][3]   no longer viable

---

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18. 09. 2001  |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Welgla 12, 53-114 WROCŁAW, POLAND

NAME AND ADDRESS OF DEPOSITOR

RECEIPT IN THE CASE OF AN ORIGINAL DEPOSIT issued pursuant to Rule 7.1 by the INTERNATIONAL DEPOSITARY AUTHORITY identified at the bottom of this page

| I. IDENTIFICATION OF THE MICROORGANISM | |
|---|---|
| Identification reference given by the DEPOSITOR: <br><br> P2 | Accession number given by the INTERNATIONAL DEPOSITARY AUTHORITY: <br><br> F/00009 |

| II. SCIENTIFIC DESCRIPTION AND/OR PROPOSED TAXONOMIC DESIGNATION |
|---|
| The microorganism identified under I above was accompanied by: <br><br> ☐ a scientific description <br><br> ☒ a proposed taxonomic designation    Myoviridae MI3 <br><br> (Mark with a cross where applicable) |

| III. RECEIPT AND ACCEPTANCE |
|---|
| This International Depositary Authority accepts the microorganism identified under I above, which was received by it on (date of the original deposit)[1]  18.07.2001 |

| IV. INTERNATIONAL DEPOSITARY AUTHORITY | |
|---|---|
| Name: Polish Collection of Microorganisms <br> Address: LUDWIK HIRSZFELD INSTITUTE <br> OF IMMUNOLOGY AND EXPERIMENTAL THERAPY <br> Polish Academy of Sciences <br> Rudolfa Welgla 12, 53-114 WROCŁAW, POLAND | Signature(s) of person(s) having the power to represent the International Depositary Authority or of authorized official(s): <br><br> Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND |
|---|---|

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND Address: | Accession number given by the POLISH COLLECTION OF MICROORGANISMS F/00009 Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X] [3] viable<br><br>[ ] [3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br><br><br>Date: 13. 03. 2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|---|

| I. IDENTIFICATION OF THE MICROORGANISM ||
|---|---|
| Identification reference given by the DEPOSITOR:<br><br>P3 | Accession number given by the INTERNATIONAL DEPOSITARY AUTHORITY:<br><br>F/00010 |
| II. SCIENTIFIC DESCRIPTION AND/OR PROPOSED TAXONOMIC DESIGNATION ||
| The microorganism identified under I above was accompanied by:<br><br>☐     a scientific description<br><br>☒     a proposed taxonomic designation     Myoviridae MI9<br>(Mark with a cross where applicable) ||
| III. RECEIPT AND ACCEPTANCE ||
| This International Depositary Authority accepts the microorganism identified under I above, which was received by it on (date of the original deposit)¹     18.07.2001 ||
| IV. INTERNATIONAL DEPOSITARY AUTHORITY ||
| Name: Polish Collection of Microorganisms<br><br>Address:    LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):<br><br>Date: 16.09.2001 |

¹ Where Rule 6.4 (d) applies, such date is the date on which the statut of International depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND |
|---|---|

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Address: Rudolfa Weigla 12, 53-114 WROCLAW, POLAND | Accession number given by the POLISH COLLECTION OF MICROORGANISMS F/00010 Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X][3]   viable<br><br>[ ][3]   no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| | |
| V. INTERNATIONAL DEPOSITARY AUTHORITY | |
| Name: Polish Collection of Microorganisms<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18, 09, 2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR: P4 | Accession number given by the INTERNATIONAL DEPOSITARY AUTHORITY: F/00011 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☒ a proposed taxonomic designation Myoviridae MI3 <br> (Mark with a cross where applicable) |

| III. RECEIPT AND ACCEPTANCE |
|---|
| This International Depositary Authority accepts the microorganism identified under I above, which was received by it on (date of the original deposit)¹ 18.07.2001 |

| IV. INTERNATIONAL DEPOSITARY AUTHORITY | |
|---|---|
| Name: Polish Collection of Microorganisms <br> Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s): <br> Date: |

¹ Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS<br>F/00011<br>Date of the deposit or of the transfer:<br>18.07.2001 |

| III. VIABILITY STATEMENT |
|---|
| The viability of the microorganism identified under II above was tested on 1.09.2001 [2]. On that date, the said microorganism was<br>[X][3] viable<br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>LUDWIK HIRSZFELD INSTITUTE<br>Address: OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

| I. IDENTIFICATION OF THE MICROORGANISM ||
|---|---|
| Identification reference given by the DEPOSITOR:<br>P5 | Accession number given by the INTERNATIONAL DEPOSITARY AUTHORITY:<br>F/00012 |
| II. SCIENTIFIC DESCRIPTION AND/OR PROPOSED TAXONOMIC DESIGNATION ||
| The microorganism identified under I above was accompanied by:<br><br>☐ a scientific description<br><br>☒ a proposed taxonomic designation  Mvoviridae MI9<br>(Mark with a cross where applicable) ||
| III. RECEIPT AND ACCEPTANCE ||
| This International Depositary Authority accepts the microorganism identified under I above, which was received by it on (date of the original deposit)[1]  18.07.2001 ||
| IV. INTERNATIONAL DEPOSITARY AUTHORITY ||
| Name: Polish Collection of Microorganisms<br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 13.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Address: Rudolfa Weigla 12, 53-114 WROCŁAW, POLAND | Accession number given by the POLISH COLLECTION OF MICROORGANISMS F/00012 Date of the deposit or of the transfer: 18.07.2001 |

III. VIABILITY STATEMENT

The viability of the microorganism identified under II above was tested
on   1.09.2001   [2]. On that date, the said microorganism was

[X][3]   viable

[ ][3]   no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

| I. IDENTIFICATION OF THE MICROORGANISM | |
|---|---|
| Identification reference given by the DEPOSITOR:<br><br>P6 | Accession number given by the INTERNATIONAL DEPOSITARY AUTHORITY:<br><br>F/00013 |

| II. SCIENTIFIC DESCRIPTION AND/OR PROPOSED TAXONOMIC DESIGNATION |
|---|
| The microorganism identified under I above was accompanied by:<br><br>☐     a scientific description<br><br>[X]     a proposed taxonomic designation     Myoviridae MI3<br>(Mark with a cross where applicable) |

| III. RECEIPT AND ACCEPTANCE |
|---|
| This International Depositary Authority accepts the microorganism identified under I above, which was received by it on (date of the original deposit)[1]    18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[1] Where Rule 6.4 (d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF THE PARTY TO WHOM THE VIABILITY STATEMENT IS ISSUED | VIABILITY STATEMENT<br>issued pursuant to Rule 10.2 by the<br>INTERNATIONAL DEPOSITARY AUTHORITY<br>identified on the following page |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY<br>Polish Academy of Sciences<br>Address: Rudolfa Weigla 12, 53-114 WROCŁAW, POLAND | Accession number given by the<br>POLISH COLLECTION OF MICROORGANISMS<br>F/00013<br>Date of the deposit or of the transfer:<br>18.07.2001 |

| III. VIABILITY STATEMENT |
|---|
| The viability of the microorganism identified under II above was tested<br>on 1.09.2001 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

| I. IDENTIFICATION OF THE MICROORGANISM ||
|---|---|
| Identification reference given by the DEPOSITOR:<br><br>P7 | Accession number given by the INTERNATIONAL DEPOSITARY AUTHORITY:<br><br>F/00014 |

| II. SCIENTIFIC DESCRIPTION AND/OR PROPOSED TAXONOMIC DESIGNATION |
|---|
| The microorganism identified under I above was accompanied by:<br><br>☐    a scientific description<br><br>[X]    a proposed taxonomic designation    Myoviridae MI9<br>(Mark with a cross where applicable) |
| III. RECEIPT AND ACCEPTANCE |
| This International Depositary Authority accepts the microorganism identified under I above, which was received by it on (date of the original deposit)¹    18.07.2001 |

| IV. INTERNATIONAL DEPOSITARY AUTHORITY ||
|---|---|
| Name: Polish Collection of Microorganisms<br>LUDWIK HIRSZFELD INSTITUTE<br>Address: OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.07.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND  NAME AND ADDRESS OF THE PARTY TO WHOM THE VIABILITY STATEMENT IS ISSUED |
|---|---|

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences  Address: Rudolfa Weigla 12, 53-114 WROCLAW, POLAND | Accession number given by the POLISH COLLECTION OF MICROORGANISMS F/00014 Date of the deposit or of the transfer: 18.07.2001 |

| III. VIABILITY STATEMENT |
|---|
| The viability of the microorganism identified under II above was tested on 1.09.2001 [2]. On that date, the said microorganism was  [X][3] viable  [ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
|  |  |
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rodolfa Weigla 12, 53-114 WROCLAW, POLAND | Signature(s) of person(s) having the power to represent the International Depositary Authority or of authorized official(s):<br><br>Date: 15.09.2001 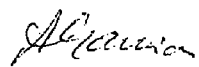 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR: P8 | Accession number given by the INTERNATIONAL DEPOSITARY AUTHORITY: F/00015 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation  Podoviridae P13<br>(Mark with a cross where applicable) |

| III. RECEIPT AND ACCEPTANCE |
|---|
| This International Depositary Authority accepts the microorganism identified under I above, which was received by it on (date of the original deposit)[1]   18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00015<br>Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X] [3]   viable<br><br>[ ] [3]   no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18. 09. 2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|

| I. IDENTIFICATION OF THE MICROORGANISM ||
|---|---|
| Identification reference given by the DEPOSITOR:<br><br>P9 | Accession number given by the INTERNATIONAL DEPOSITARY AUTHORITY:<br><br>F/00016 |
| II. SCIENTIFIC DESCRIPTION AND/OR PROPOSED TAXONOMIC DESIGNATION ||
| The microorganism identified under I above was accompanied by:<br><br>☐ a scientific description<br><br>[X] a proposed taxonomic designation   Myoviridae MI3<br>(Mark with a cross where applicable) ||
| III. RECEIPT AND ACCEPTANCE ||
| This International Depositary Authority accepts the microorganism identified under I above, which was received by it on 18.07.2001 (date of the original deposit)[1] ||
| IV. INTERNATIONAL DEPOSITARY AUTHORITY ||
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | VIABILITY STATEMENT issued pursuant to Rule 10.2 by the INTERNATIONAL DEPOSITARY AUTHORITY identified on the following page |
| NAME AND ADDRESS OF THE PARTY TO WHOM THE VIABILITY STATEMENT IS ISSUED | |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00016<br>Date of the deposit or of the transfer:<br>18.07.2001 |

III. VIABILITY STATEMENT

The viability of the microorganism identified under II above was tested
on  1.09.2001  [2]. On that date, the said microorganism was

[X][3]  viable

[ ][3]  no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] ||
|---|---|
| V. INTERNATIONAL DEPOSITARY AUTHORITY ||
| Name: Polish Collection of Microorganism<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF DEPOSITOR

RECEIPT IN THE CASE OF AN ORIGINAL DEPOSIT issued pursuant to Rule 7.1 by the INTERNATIONAL DEPOSITARY AUTHORITY identified at the bottom of this page

| I. IDENTIFICATION OF THE MICROORGANISM | |
|---|---|
| Identification reference given by the DEPOSITOR: <br> P10 | Accession number given by the INTERNATIONAL DEPOSITARY AUTHORITY: <br> F/00017 |

| II. SCIENTIFIC DESCRIPTION AND/OR PROPOSED TAXONOMIC DESIGNATION |
|---|
| The microorganism identified under I above was accompanied by: <br><br> ☐ a scientific description <br><br> ☒ a proposed taxonomic designation   Myoviridae MI3 <br> (Mark with a cross where applicable) |

| III. RECEIPT AND ACCEPTANCE |
|---|
| This International Depositary Authority accepts the microorganism identified under I above, which was received by it on (date of the original deposit)[1]   18.07.2001 |

| IV. INTERNATIONAL DEPOSITARY AUTHORITY | |
|---|---|
| Name: Polish Collection of Microorganisms <br><br> Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s): <br><br> Date: |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF THE PARTY TO WHOM THE VIABILITY STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCLAW, POLAND | Accession number given by the POLISH COLLECTION OF MICROORGANISMS F/00017<br>Date of the deposit or of the transfer: 18.07.2001 |
| III. VIABILITY STATEMENT | |
| The viability of the microorganism identified under II above was tested on 1.09.2001 [1]. On that date, the said microorganism was<br><br>[X][3] viable<br><br>[ ][3] no longer viable | |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

V. INTERNATIONAL DEPOSITARY AUTHORITY

| | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18.09. 2001 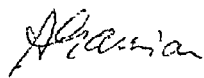 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND  NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|---|

| I. IDENTIFICATION OF THE MICROORGANISM | |
|---|---|
| Identification reference given by the DEPOSITOR:  P11 | Accession number given by the INTERNATIONAL DEPOSITARY AUTHORITY:  F/00018 |

| II. SCIENTIFIC DESCRIPTION AND/OR PROPOSED TAXONOMIC DESIGNATION |
|---|
| The microorganism identified under I above was accompanied by:  ☐      a scientific description  ☒      a proposed taxonomic designation    Myoviridae MI3  (Mark with a cross where applicable) |

| III. RECEIPT AND ACCEPTANCE |
|---|
| This International Depositary Authority accepts the microorganism identified under I above, which was received by it on (date of the original deposit)[1]    18.07.2001 |

| IV. INTERNATIONAL DEPOSITARY AUTHORITY | |
|---|---|
| Name: Polish Collection of Microorganisms  Address: LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND | Signature(s) of person(s) having the power to represent the International Depositary Authority or of authorized official(s):  Date: 18. 09. 2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF THE PARTY TO WHOM THE VIABILITY STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00018<br>Date of the deposit or of the transfer: 18.07.2001 |

III. VIABILITY STATEMENT

The viability of the microorganism identified under II above was tested
on  1.09.2001  [2]. On that date, the said microorganism was

[X][3]  viable

[ ][3]  no longer viable

---

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganism<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001  |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF DEPOSITOR

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br><br> P12 | Accession number given by the INTERNATIONAL DEPOSITARY AUTHORITY: <br><br> F/00019 |
| II. SCIENTIFIC DESCRIPTION AND/OR PROPOSED TAXONOMIC DESIGNATION | |
| The microorganism identified under I above was accompanied by: <br><br> ☐ a scientific description <br><br> ☒ a proposed taxonomic designation Siphoviridae SI7 <br> (Mark with a cross where applicable) | |
| III. RECEIPT AND ACCEPTANCE | |
| This International Depositary Authority accepts the microorganism identified under I above, which was received by it on (date of the original deposit)[1]  18.07.2001 | |
| IV. INTERNATIONAL DEPOSITARY AUTHORITY | |
| Name: Polish Collection of Microorganisms <br><br> Address: LUDWIK HIRSZFELD INSTITUTE <br> OF IMMUNOLOGY AND EXPERIMENTAL THERAPY <br> Polish Academy of Sciences <br> Rudolfa Weigla 12, 53-114 WROCLAW, POLAND | Signature(s) of person(s) having the power to represent the International Depositary Authority or of authorized official(s): <br><br> Date: 18.07.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS<br>F/00019<br>Date of the deposit or of the transfer:<br>18.07.2001 |

| III. VIABILITY STATEMENT |
|---|
| The viability of the microorganism identified under II above was tested on 1.09.2001 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>P13 | Accession number given by the INTERNATIONAL DEPOSITARY AUTHORITY:<br><br>F/00020 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation   Podoviridae PI1<br>(Mark with a cross where applicable) |

| III. RECEIPT AND ACCEPTANCE |
|---|
| This International Depositary Authority accepts the microorganism identified under I above, which was received by it on (date of the original deposit)[1]   18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY<br>Polish Academy of Sciences<br>Rudolfa Weigla 12, 53-114 WROCLAW, POLAND<br><br>NAME AND ADDRESS OF THE PARTY TO WHOM THE VIABILITY STATEMENT IS ISSUED | VIABILITY STATEMENT<br>issued pursuant to Rule 10.2 by the<br>INTERNATIONAL DEPOSITARY AUTHORITY<br>identified on the following page |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY<br>Polish Academy of Sciences<br>Address: Rudolfa Weigla 12, 53-114 WROCLAW, POLAND | Accession number given by the POLISH COLLECTION OF MICROORGANISMS<br>F/00020<br>Date of the deposit or of the transfer:<br>18.07.2001 |

III. VIABILITY STATEMENT

The viability of the microorganism identified under II above was tested on 1.09.2001 [2]. On that date, the said microorganism was

[X] [3] viable

[ ] [3] no longer viable

---

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] ||
|---|---|
| V. INTERNATIONAL DEPOSITARY AUTHORITY ||
| Name: Polish Collection of Microorganisms<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.03.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF DEPOSITOR

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br><br> P14 | Accession number given by the INTERNATIONAL DEPOSITARY AUTHORITY: <br><br> F/00021 |
| II. SCIENTIFIC DESCRIPTION AND/OR PROPOSED TAXONOMIC DESIGNATION | |
| The microorganism identified under I above was accompanied by: <br><br> ☐     a scientific description <br><br> ☒     a proposed taxonomic designation Myoviridae MI3 <br> (Mark with a cross where applicable) | |
| III. RECEIPT AND ACCEPTANCE | |
| This International Depositary Authority accepts the microorganism identified under I above, which was received by it on (date of the original deposit)¹    18.07.2001 | |
| IV. INTERNATIONAL DEPOSITARY AUTHORITY | |
| Name: Polish Collection of Microorganisms <br><br> Address: LUDWIK HIRSZFELD INSTITUTE <br> OF IMMUNOLOGY AND EXPERIMENTAL THERAPY <br> Polish Academy of Sciences <br> Rudolfa Weigla 12, 53-114 WROCLAW, POLAND | Signature(s) of person(s) having the power to represent the International Depositary Authority or of authorized official(s): <br><br> Date: 18.09.2001 |

¹ Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCLAW, POLAND | Accession number given by the POLISH COLLECTION OF MICROORGANISMS F/00021<br>Date of the deposit or of the transfer: 18.07.2001 |

| III. VIABILITY STATEMENT |
|---|
| The viability of the microorganism identified under II above was tested<br>on 1.09.2001 [2]. On that date, the said microorganism was<br>[X] [3] viable<br>[ ] [3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001  |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF DEPOSITOR

RECEIPT IN THE CASE OF AN ORIGINAL DEPOSIT issued pursuant to Rule 7.1 by the INTERNATIONAL DEPOSITARY AUTHORITY identified at the bottom of this page

| I. IDENTIFICATION OF THE MICROORGANISM | |
|---|---|
| Identification reference given by the DEPOSITOR: P15 | Accession number given by the INTERNATIONAL DEPOSITARY AUTHORITY: F/00022 |

| II. SCIENTIFIC DESCRIPTION AND/OR PROPOSED TAXONOMIC DESIGNATION |
|---|
| The microorganism identified under I above was accompanied by: |
| ☐ a scientific description |
| ☒ a proposed taxonomic designation  Myoviridae MI3 |
| (Mark with a cross where applicable) |

| III. RECEIPT AND ACCEPTANCE |
|---|
| This International Depositary Authority accepts the microorganism identified under I above, which was received by it on (date of the original deposit)[1]     18.07.2001 |

| IV. INTERNATIONAL DEPOSITARY AUTHORITY | |
|---|---|
| Name: Polish Collection of Microorganisms<br>Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s):<br>Date: 18.07.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCLAW, POLAND | Accession number given by the POLISH COLLECTION OF MICROORGANISMS<br>F/00022<br>Date of the deposit or of the transfer:<br>18.07.2001 |
| III. VIABILITY STATEMENT ||
| The viability of the microorganism identified under II above was tested on 1.09.2001     [2]. On that date, the said microorganism was<br><br>[X] [3]   viable<br><br>[ ] [3]   no longer viable ||

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| V. INTERNATIONAL DEPOSITARY AUTHORITY | |
| Name: Polish Collection of Microorganisms<br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18. 09. 2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>P16 | Accession number given by the INTERNATIONAL DEPOSITARY AUTHORITY:<br><br>F/00023 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation  Myoviridae MI3<br>(Mark with a cross where applicable) |

| III. RECEIPT AND ACCEPTANCE |
|---|
| This International Depositary Authority accepts the microorganism identified under I above, which was received by it on (date of the original deposit)¹    18.07.2001 |

| IV. INTERNATIONAL DEPOSITARY AUTHORITY | |
|---|---|
| Name: Polish Collection of Microorganisms<br>Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s):<br><br>Date: 18.09.2001 |

¹ Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCŁAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCŁAW, POLAND | Accession number given by the POLISH COLLECTION OF MICROORGANISMS F/00023<br>Date of the deposit or of the transfer: 18.07.2001 |

III. VIABILITY STATEMENT

The viability of the microorganism identified under II above was tested on 1.09.2001 [2]. On that date, the said microorganism was

[X] [3] viable

[ ] [3] no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.07.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>P17 | Accession number given by the INTERNATIONAL DEPOSITARY AUTHORITY:<br><br>F/00024 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation    Siphoviridae SII2<br>(Mark with a cross where applicable) |

| III. RECEIPT AND ACCEPTANCE |
|---|
| This International Depositary Authority accepts the microorganism identified under I above, which was received by it on (date of the original deposit)[1]    18.07.2001 |

| IV. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCŁAW, POLAND NAME AND ADDRESS OF THE PARTY TO WHOM THE VIABILITY STATEMENT IS ISSUED |
|---|---|

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences Address: Rudolfa Weigla 12, 53-114 WROCŁAW, POLAND | Accession number given by the POLISH COLLECTION OF MICROORGANISMS F/00024 Date of the deposit or of the transfer: 18.07.2001 |

| III. VIABILITY STATEMENT |
|---|
| The viability of the microorganism identified under II above was tested on 1.09.2001 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 13.09. 2001 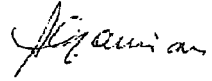 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br>P18 | Accession number given by the INTERNATIONAL DEPOSITARY AUTHORITY:<br>F/00025 |

| II. SCIENTIFIC DESCRIPTION AND/OR PROPOSED TAXONOMIC DESIGNATION |
|---|
| The microorganism identified under I above was accompanied by:<br><br>☐ a scientific description<br><br>☒ a proposed taxonomic designation    Myoviridae MI3<br>(Mark with a cross where applicable) |

| III. RECEIPT AND ACCEPTANCE |
|---|
| This International Depositary Authority accepts the microorganism identified under I above, which was received by it on (date of the original deposit)[1]   18.07.2001 |

| IV. INTERNATIONAL DEPOSITARY AUTHORITY | |
|---|---|
| Name:    Polish Collection of Microorganisms<br>         LUDWIK HIRSZFELD INSTITUTE<br>Address: OF IMMUNOLOGY AND EXPERIMENTAL THERAPY<br>         Polish Academy of Sciences<br>         Rudolfa Weigla 12, 53-114 WROCLAW, POLAND | Signature(s) of person(s) having the power to represent the International Depositary Authority or of authorized official(s):<br><br>Date: 18.09.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCLAW, POLAND | Accession number given by the POLISH COLLECTION OF MICROORGANISMS F/00025<br>Date of the deposit or of the transfer:<br>18.07.2001 |

III. VIABILITY STATEMENT

The viability of the microorganism identified under II above was tested
on    1.09.2001    [2]. On that date, the said microorganism was

[x][3]   viable

[ ][3]   no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL
RECOGNITION OF THE DEPOSIT OF MICROORGANISMS
FOR THE PURPOSE OF PATENT PROCEDURE

INTERNATIONAL FORM

| TO | LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:  P19 | Accession number given by the INTERNATIONAL DEPOSITARY AUTHORITY:  F/00026 |

| II. SCIENTIFIC DESCRIPTION AND/OR PROPOSED TAXONOMIC DESIGNATION |
|---|
| The microorganism identified under I above was accompanied by: <br> ☐  a scientific description <br> ☒  a proposed taxonomic designation   Myoviridae MI3 <br> (Mark with a cross where applicable) |

| III. RECEIPT AND ACCEPTANCE |
|---|
| This International Depositary Authority accepts the microorganism identified under I above, which was received by it on (date of the original deposit)[1]    18.07.2001 |

| IV. INTERNATIONAL DEPOSITARY AUTHORITY | |
|---|---|
| Name: Polish Collection of Microorganisms <br> Address: LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | Signature(s) of person(s) having the power to represent the International Depositary Authority or of authorized official(s): <br><br> Date: |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO | |
|---|---|
| LUDWIK HIRSZFELD INSTITUTE OF IMMUNOLOGY AND EXPERIMENTAL THERAPY Polish Academy of Sciences Rudolfa Weigla 12, 53-114 WROCLAW, POLAND | VIABILITY STATEMENT issued pursuant to Rule 10.2 by the INTERNATIONAL DEPOSITARY AUTHORITY identified on the following page |
| NAME AND ADDRESS OF THE PARTY TO WHOM THE VIABILITY STATEMENT IS ISSUED | |

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY<br>Address: Polish Academy of Sciences Rudolfa Weigla 12, 53-114 WROCLAW, POLAND | Accession number given by the POLISH COLLECTION OF MICROORGANISMS F/00026<br>Date of the deposit or of the transfer:<br>18.07.2001 |

III. VIABILITY STATEMENT

The viability of the microorganism identified under II above was tested
on   1.09.2001                      [2]. On that date, the said microorganism was

[X][3]   viable

[ ][3]   no longer viable

---

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] | |
|---|---|
| | |
| V. INTERNATIONAL DEPOSITARY AUTHORITY | |
| Name: Polish Collection of Microorganisms<br><br>Address: LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 18.09.2001 |

[4] Fill in if the information has been requested and if the results of the test were negative.

BUDAPEST TREATY ON THE INTERNATIONAL RECOGNITION OF THE DEPOSIT OF MICROORGANISMS FOR THE PURPOSE OF PATENT PROCEDURE

INTERNATIONAL FORM

| TO<br>LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND<br><br>NAME AND ADDRESS OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|

| I. IDENTIFICATION OF THE MICROORGANISM ||
|---|---|
| Identification reference given by the DEPOSITOR:<br><br>P20 | Accession number given by the INTERNATIONAL DEPOSITARY AUTHORITY:<br><br>F/00027 |
| II. SCIENTIFIC DESCRIPTION AND/OR PROPOSED TAXONOMIC DESIGNATION ||
| The microorganism identified under I above was accompanied by:<br><br>☐ a scientific description<br><br>☒ a proposed taxonomic designation    Myoviridae MI9<br>(Mark with a cross where applicable) ||
| III. RECEIPT AND ACCEPTANCE ||
| This International Depositary Authority accepts the microorganism identified under I above, which was received by it on (date of the original deposit)[1]    18.07.2001 ||
| IV. INTERNATIONAL DEPOSITARY AUTHORITY ||
| Name: Polish Collection of Microorganisms<br><br>Address:   LUDWIK HIRSZFELD INSTITUTE<br>OF IMMUNOLOGY AND EXPERIMENTAL THERAPY<br>Polish Academy of Sciences<br>Rudolfa Weigla 12, 53-114 WROCŁAW, POLAND | Signature(s) of person(s) having the power to represent the International Depositary Authority or of authorized official(s):<br><br>Date: 18.04.2001 |

[1] Where Rule 6.4 (d) applies, such date is the date on which the statut of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
LUDWIK HIRSZFELD INSTITUTE
OF IMMUNOLOGY AND EXPERIMENTAL THERAPY
Polish Academy of Sciences
Rudolfa Weigla 12, 53-114 WROCLAW, POLAND

NAME AND ADDRESS OF
THE PARTY TO WHOM THE VIABILITY
STATEMENT IS ISSUED

VIABILITY STATEMENT
issued pursuant to Rule 10.2 by the
INTERNATIONAL DEPOSITARY AUTHORITY
identified on the following page

| I. DEPOSITOR | II. IDENTIFICATION OF THE MICROORGANISM |
|---|---|
| Name: LUDWIK HIRSZFELD INSTITUTE OF IMMUNOLOGY AND EXPERIMENTAL THERAPY Polish Academy of Sciences<br>Address: Rudolfa Weigla 12, 53-114 WROCLAW, POLAND | Accession number given by the POLISH COLLECTION OF MICROORGANISMS<br>F/00027<br>Date of the deposit or of the transfer:<br>18.07.2001 |

III. VIABILITY STATEMENT

The viability of the microorganism identified under II above was tested
on    1.09.2001       [2]. On that date, the said microorganism was

[X][3]   viable

[ ][3]   no longer viable

[1] Indicate the date of the original deposit or, where a new deposit or a transfer has been made, the most recent relevant date (date of the new deposit or date of the transfer).

[2] In the cases referred to in Rule 10.2 (a) (ii) and (iii), refer to the most recent viability test.

[3] Mark with a cross the applicable box.

| IV. CONDITIONS UNDER WHICH THE VIABILITY TEST HAS BEEN PERFORMED[4] |  |
|---|---|
| V. INTERNATIONAL DEPOSITARY AUTHORITY | |
| Name: Polish Collection of Microorganisms<br><br>Address: LUDWIK HIRSZFELD INSTITUTE OF IMMUNOLOGY AND EXPERIMENTAL THERAPY<br>Polish Academy of Sciences<br>Rudolfa Weigla 12, 53-114 WROCLAW, POLAND | Signature(s) of person(s) having the power to represent the International Depositary Authority or of authorized official(s):<br><br>Date: 13.09.2001 |

[4] Fill in if the information has been requested and if the results of the test were negative.

The invention claimed is:

1. A pharmaceutical composition comprising a multivalent bacteriophage strain deposited with the Polish Collection or Microorganisms selected from the group consisting of PCM F/00001, PCM F/00002, PCM F/00003, PCM F/00004, PCM F/00005, PCM F/00006, and PCM F/00007.

2. The pharmaceutical composition of claim 1 comprising bacteriophage strains PCM F/00001, PCM F/00002, and PCM F/00004 or PCM F/00005.

3. The pharmaceutical composition of claim 1 comprising at least one bacteriophage strain selected from the group consisting of PCM F/00002, PCM F/00004, and PCM F/00007.

4. A pharmaceutical composition comprising a bacteriophage strain deposited with the Polish Collection of Microorganisms selected from the group consisting of PCM F/00008, PCM F/00009, PCM F/00010, PCM F/00011, PCM F/00012, PCM F/00013, PCM F/00014, PCM F/00015, PCM F/00016, PCM F/00017, PCM F/00018, PCM F/00019, PCM F/00020, PCM F/00021, PCM F/00022, PCM F/00023, PCM F/00024, PCM F/00025, PCM F/00026, and PCM F/00027.

5. The pharmaceutical composition of claim 4 comprising bacteriophage strains PCM F/00014, PCM F/00027, and PCM F/00013.

6. The pharmaceutical composition of claim 4 comprising at least one bacteriophage strain selected from the group consisting of PCM F/00010, PCM F/00013, and PCM F/00018.

7. A multivalent bacteriophage strain deposited with the Polish Collection of Microorganisms selected from the group consisting of PCM F/00001, PCM F/00002, PCM F/00003, PCM F/00004, PCM F/00005, PCM F/00006, and PCM F/00007.

8. A multivalent bacteriophage strain deposited with the Polish Collection of Microorganisms selected from the group consisting of PCM F/00008, PCM F/00009, PCM F/00010, PCM F/00011, PCM F/00012, PCM F/00013, PCM F/00014, PCM F/00015, PCM F/00016, PCM F/00017, PCM F/00018, PCM F/00019, PCM F/00020, PCM F/00021, PCM F/00022, PCM F/00023, PCM F/00024, PCM F/00025, PCM F/00026, and PCM F/00027.

\* \* \* \* \*